(12) United States Patent
Furuhashi et al.

(10) Patent No.: US 12,102,745 B2
(45) Date of Patent: Oct. 1, 2024

(54) BLOOD PURIFICATION DEVICE

(71) Applicant: Nikkiso Company Limited, Tokyo (JP)

(72) Inventors: Tomohiro Furuhashi, Shizuoka (JP); Hideto Maki, Shizuoka (JP); Ferenc Kazinczi, Shizuoka (JP); Yuki Eda, Shizuoka (JP); Kenji Furuhashi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 484 days.

(21) Appl. No.: 17/418,014

(22) PCT Filed: Aug. 29, 2019

(86) PCT No.: PCT/JP2019/033856
§ 371 (c)(1),
(2) Date: Jun. 24, 2021

(87) PCT Pub. No.: WO2020/136999
PCT Pub. Date: Jul. 2, 2020

(65) Prior Publication Data
US 2022/0088281 A1 Mar. 24, 2022

(30) Foreign Application Priority Data
Dec. 28, 2018 (JP) .................. 2018-248124

(51) Int. Cl.
*A61M 1/36* (2006.01)
*B01D 19/00* (2006.01)

(52) U.S. Cl.
CPC ........ *A61M 1/3643* (2013.01); *A61M 1/3624* (2013.01); *A61M 1/3638* (2014.02);
(Continued)

(58) Field of Classification Search
CPC .............. A61M 1/3624; A61M 1/3627; A61M 1/3638; A61M 1/3643; A61M 1/3646;
(Continued)

(56) References Cited

U.S. PATENT DOCUMENTS 8,834,399 B2 * 9/2014 Muller-Spanka ... A61M 1/3627
604/4.01
2012/0061320 A1 3/2012 Nuernberger et al.
(Continued)

FOREIGN PATENT DOCUMENTS

CN 102427835 A 4/2012
EP 2883558 A1 6/2015
(Continued)

OTHER PUBLICATIONS

European Search Report for Application No. 19904794.5, dated Sep. 7, 2022, 7 pgs.
(Continued)

*Primary Examiner* — Terry K Cecil
(74) *Attorney, Agent, or Firm* — Young Basile Hanlon & MacFarlane, P.C.

(57) ABSTRACT

A blood purification device includes a blood circuit for extracorporeally circulating blood of a patient: a blood purifier provided on the blood circuit; a gas-liquid separator being provided on the blood circuit on the downstream side of the blood purifier on a blood flow and separating air bubbles contained in inflowing blood: and a liquid level adjustment unit capable of adjusting a liquid level height in the gas-liquid separator. The liquid level adjustment unit performs control so that the liquid level height during priming is higher than the liquid level height during treatment.

12 Claims, 5 Drawing Sheets

(52) U.S. Cl.
CPC ..... *B01D 19/0031* (2013.01); *B01D 19/0063* (2013.01); *A61M 2205/07* (2013.01); *A61M 2205/3331* (2013.01); *A61M 2205/3375* (2013.01); *A61M 2205/3382* (2013.01); *A61M 2205/3386* (2013.01)

(58) Field of Classification Search
CPC ...... A61M 2205/07; A61M 2205/3331; A61M 2205/3375; A61M 2205/3382; A61M 2205/3386; B01D 19/0031; B01D 19/0063
See application file for complete search history.

(56) References Cited

U.S. PATENT DOCUMENTS

| | | | | |
|---|---|---|---|---|
| 2015/0151036 | A1* | 6/2015 | Furuhashi | A61M 1/3644 |
| | | | | 210/138 |
| 2018/0036472 | A1 | 2/2018 | Kelly et al. | |

FOREIGN PATENT DOCUMENTS

| | | |
|---|---|---|
| JP | 8-57043 A | 3/1996 |
| JP | H08-057043 A | 3/1996 |
| JP | 2006-263136 A | 10/2006 |
| JP | 2013-106976 A | 6/2013 |
| JP | 2017-217161 A | 12/2017 |

OTHER PUBLICATIONS

International Search Report for Application No. PCT/JP2019/033856, dated Nov. 19, 2019.
Japanese Office Action for Application No. 2018-248124, dated Jun. 28, 2022, with English translation.
Chinese Office Action for Application No. 201980086049.4, dated Nov. 17, 2023, with English translation, 14 pgs.
Chinese Second Office Action for Application No. 201980085954, dated May 28, 2024, with English translation, 19 pgs.

* cited by examiner

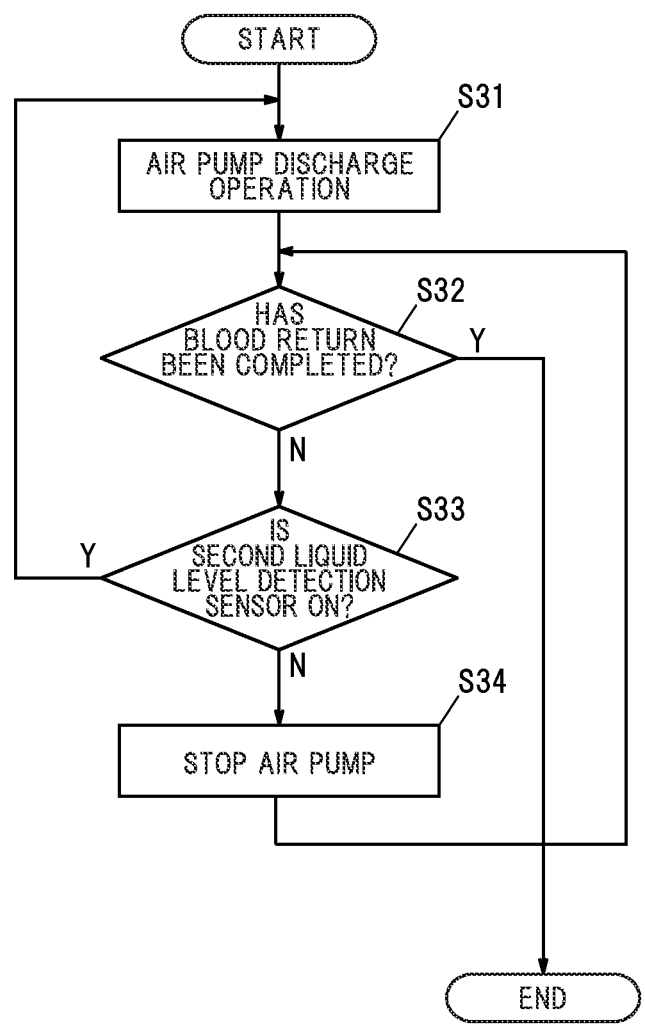

BLOOD PURIFICATION DEVICE

CROSS-REFERENCE TO RELATED APPLICATION(S)

This application is a national stage entry of International Application No. PCT/JP2019/033856, filed on Aug. 29, 2019, which claims priority to Japanese Application No. 2018-248124, filed on Dec. 28, 2018, the entire disclosures of which are hereby incorporated by reference.

TECHNICAL FIELD

The invention relates to a blood purification device.

BACKGROUND ART

A blood purification device is known, which is provided with a gas-liquid separator (also called an air trap chamber) for separating and removing air bubbles from blood to suppress inclusion of air bubbles in the blood returning to a patient.

Patent Document 1 can be found as prior art document information related to the invention of the present application.

CITATION LIST

Patent Literature

Patent Document 1: JP2013/106976A

SUMMARY OF INVENTION

Technical Problem

With the blood purification device, priming for introducing a physiological saline solution into a blood circuit, etc., is performed before treatment. A liquid level height during this priming is desirably as high as possible so that the gas-liquid separator is cleaned to the upper part. However, if the liquid level height in the gas-liquid separator is set to high, the amount of blood to be extracorporeally circulated during the treatment is increased, hence, not preferable.

Conventionally, the liquid level height in the gas-liquid separator is set to a liquid level height optimum for treatment, and a worker turns the gas-liquid separator upside down during priming. However, this makes priming work complicated and improvement is thus desired.

Therefore, it is an object of the invention to provide a blood purification device capable of suppressing an increase in an amount of blood extracorporeally circulated during treatment while facilitating priming work.

Solution to Problem

The teachings herein provide a blood purification device, comprising: a blood circuit for extracorporeally circulating blood of a patient; a blood purifier provided on the blood circuit; a gas-liquid separator being provided on the blood circuit on the downstream side of the blood purifier on a blood flow and separating air bubbles contained in inflowing blood; and a liquid level adjustment unit being connected to the gas-liquid separator and being capable of adjusting a liquid level height in the gas-liquid separator, wherein the liquid level adjustment unit performs control so that the liquid level height during priming is higher than the liquid level height during treatment.

The teachings herein provide the blood purification device taught herein, wherein the liquid level adjustment unit comprises a first liquid level detection sensor being provided at a first height position of the gas-liquid separator and being capable of detecting whether a gas is present at the first height position inside the gas-liquid separator, a liquid level adjustment mechanism that can adjust the liquid level height by introducing air into the gas-liquid separator or discharging air from the gas-liquid separator, and a liquid level control unit controlling the liquid level adjustment mechanism so that, during treatment, the gas is detected at the first height position and the liquid level height is lower than the first height position, and so that, during priming, the gas is not detected at the first height position and the liquid level height is not lower than the first height position.

The teachings herein provide the blood purification device taught herein, wherein the liquid level adjustment unit further comprises a second liquid level detection sensor being provided at a second height position lower than the first height position and being capable of detecting whether a gas is present at the second height position inside the gas-liquid separator, and the liquid level control mechanism controls the liquid level adjustment mechanism so that, during treatment, the gas is not detected at the second height position and the liquid level height is lower than the first height position and not lower than the second height position, and so that, during blood return for retuning blood to a patient, the gas is detected at the second height position and the liquid level height is lower than the second height position.

The teachings herein provide the blood purification device taught herein, wherein the liquid level adjustment unit further comprises a sensor abnormality determination unit that calculates a liquid level height adjustment amount per unit time based on a history of a liquid level height adjustment operation by the liquid level adjustment mechanism, and when a result of the calculation exceeds a predetermined threshold, stops liquid level height adjustment by the liquid level adjustment mechanism upon determination that there is an abnormality in the liquid level detection sensor.

The teachings herein provide is the blood purification device taught herein, wherein the liquid level detection sensor comprises an ultrasonic sensor comprising a transmitter and a receiver that are provided so as to sandwich the gas-liquid separator, a sensor holder for holding the liquid level detection sensor is provided and attached to the gas-liquid separator, and the sensor holder is configured so that the liquid level in the gas-liquid separator can be visually checked.

The teachings herein provide is the blood purification device taught herein, wherein the sensor holder comprises a window part on the front face thereof to allow the liquid level in the gas-liquid separator to be visually checked, and the transmitter and the receiver of the ultrasonic sensor are respectively arranged on one and another of side surfaces of the sensor holder.

The teachings herein provide the blood purification device taught, wherein the liquid level adjustment unit comprises an air pump connected to the gas-liquid separator via an air filter, and a pressure sensor for detecting pressure on the air filter side of the air pump, and the liquid level adjustment mechanism further comprises a suction abnormality determination unit that stops driving the air pump when a detection value of the pressure sensor becomes lower than a preset abnormality determination pressure during when the air pump is operated to discharge the air from the gas-liquid separator.

Advantageous Effects of Invention

According to the teachings herein, it is possible to provide a blood purification device capable of suppressing an increase in an amount of blood extracorporeally circulated during treatment while facilitating priming work.

According to the teachings herein, it is possible to enhance the cleaning effect by raising the liquid level height in the gas-liquid separator during priming.

According to the teachings herein, the liquid level in the gas-liquid separator is maintained within a predetermined height range during the treatment and is lowered during the blood return, hence, an amount of a liquid such as physiological saline solution used at the time of the blood return is reduced and a blood return process can be performed in a short time.

According to the teachings herein, it is possible to detect an abnormality in the liquid level detection sensor.

According to the teachings herein, the liquid level in the gas-liquid separator can be visually checked even when an ultrasonic sensor is used as the liquid level detection sensor.

According to the teachings herein, it is possible to easily realize a configuration allowing for visual check of the liquid level in the gas-liquid separator.

According to the teachings herein, it is possible to detect abnormal suction due to wetting of the air filter.

BRIEF DESCRIPTION OF DRAWINGS

FIG. 5 is a flowchart showing the liquid level height control flow during blood return.

DESCRIPTION OF EMBODIMENT

[Embodiment] An embodiment of the invention will be described below in conjunction with the appended drawings.

Figure 1:
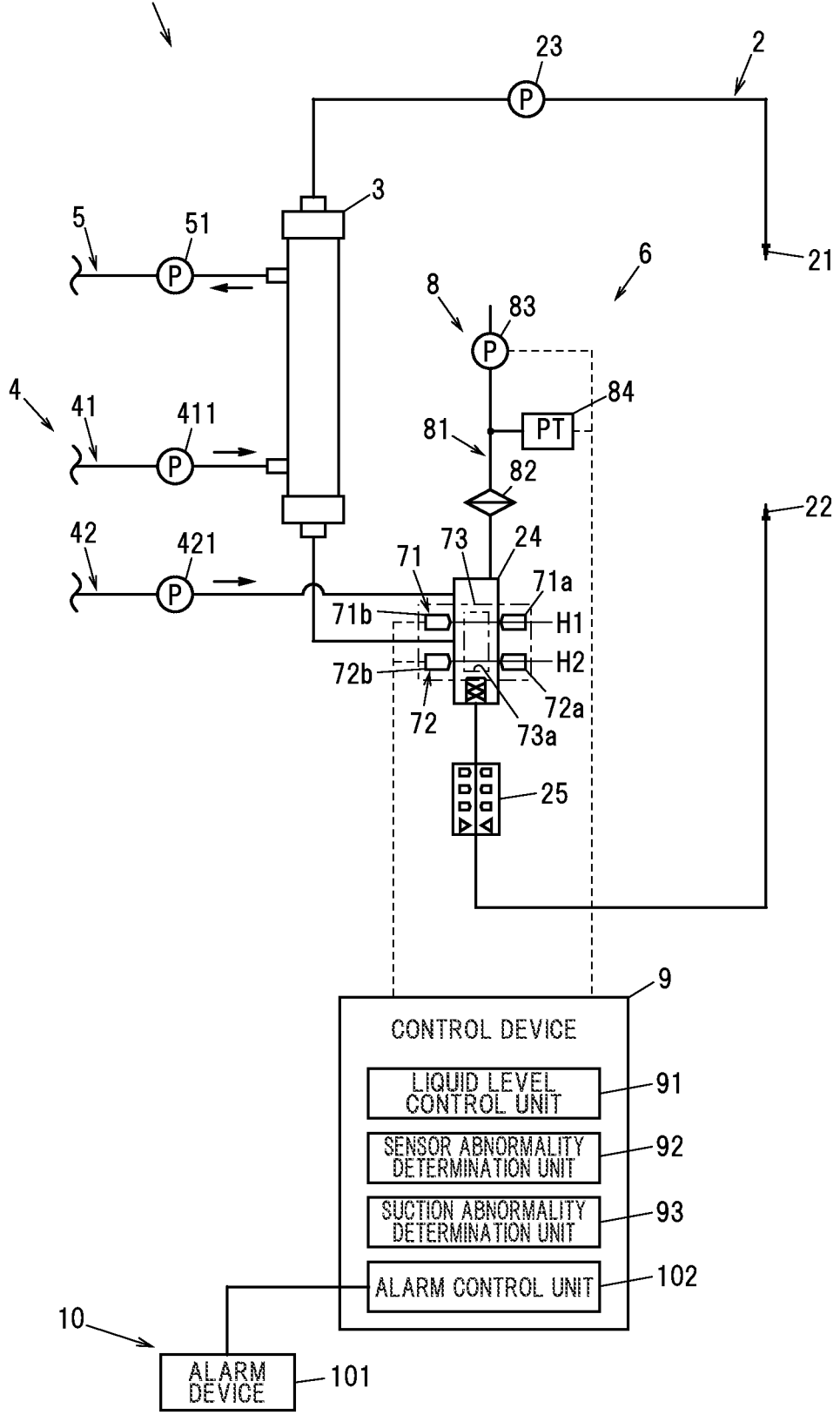
FIG. 1 is a schematic configuration diagram illustrating a blood purification device in an embodiment of the present invention.

FIG. 1 is a schematic configuration diagram illustrating a blood purification device in the present embodiment. As shown in FIG. 1, a blood purification device 1 includes a blood circuit 2 for extracorporeally circulating blood of a patient, a blood purifier 3 being provided on the blood circuit 2 and purifying the blood, liquid supply circuits 4 for supplying supply liquids to the blood purifier 3 or the blood circuit 2, and a waste liquid circuit 5 for discharging a waste liquid from the blood purifier 3.

The blood circuit 2 is composed of a flexible tube, etc. An artery-side puncture needle 21 is provided at one end of the blood circuit 2, and a vein-side puncture needle 22 is provided at the other end. In addition, a blood pump 23, the blood purifier 3, a gas-liquid separator 24 and an air bubble detector 25 are sequentially provided on the blood circuit 2 from the artery-side puncture needle 21-side toward the vein-side puncture needle 22-side. The air bubble detector 25 has an air bubble detection sensor for detecting air bubbles and a mechanism for clamping (gripping and blocking) the blood circuit 2 when air bubbles are detected.

The blood pump 23 is composed of a peristaltic pump that squeezes the tube to cause blood to flow toward the blood purifier 3. The blood purifier 3 is a device also called a dialyzer and purifies the blood by bringing the blood into contact with a dialysate through a blood purification membrane (not shown). The details of the gas-liquid separator 24 will be described later.

In the present embodiment, the blood purification device 1 has two circuits, a dialysate circuit 41 for supplying a dialysate to the blood purifier 3 and a replenishing liquid circuit 42 for directly supplying a replenishing liquid into the blood circuit 2, as the liquid supply circuits 4 so as to be able to perform various treatments. In this regard, however, the blood purification device 1 may have only one of the dialysate circuit 41 and the replenishing liquid circuit 42.

The dialysate circuit 41, the replenishing liquid circuit 42 and the waste liquid circuit 5 are each composed of a flexible tube, etc. A dialysate pump 411 composed of a peristaltic pump is provided on the dialysate circuit 41. A replacement pump 421 composed of a peristaltic pump is provided on the replenishing liquid circuit 42. A waste liquid pump 51 composed of a peristaltic pump is provided on the waste liquid circuit 5. Although the replenishing liquid circuit 42 is configured to supply the replenishing liquid to the gas-liquid separator 24 in the present embodiment, it is not limited thereto. It may be configured that the replenishing liquid is supplied to the upstream side (the artery-side puncture needle 21-side) of the blood purifier 3.

(The Gas-Liquid Separator 24 and Control of Liquid Level Therein)

The gas-liquid separator 24 is also called an air trap chamber and is configured to separate and remove air bubbles contained in inflowing blood and allows passage of only liquid toward the vein-side puncture needle 22-side. The gas-liquid separator 24 is made of, e.g., a highly transparent material such as polyvinyl chloride, polypropylene or polyethylene.

The blood purification device 1 in the present embodiment includes a liquid level adjustment unit 6 capable of adjusting a liquid level height in the gas-liquid separator 24. The liquid level adjustment mechanism 6 includes a first liquid level detection sensor 71 and a second liquid level detection sensor 72 that are provided on the gas-liquid separator 24, a liquid level adjustment mechanism 8 that can adjust the liquid level height by introducing air into the gas-liquid separator 24 or discharging air from the gas-liquid separator 24, and a control device 9 that controls the liquid level adjustment mechanism 8 to adjust the liquid level height based on detection results of both the liquid level detection sensors 71, 72.

The first liquid level detection sensor 71 is provided at a first height position H1 of the gas-liquid separator 24 and is configured to be able to detect whether a gas is present at the first height position H1 in the gas-liquid separator 24 (in other words, whether the gas-liquid separator 24 is filled with the liquid to the first height position H1). The second liquid level detection sensor 72 is provided at a second height position H2 lower than the first height position H1, and is configured to be able to detect whether a gas is present at the second height position H2 inside the gas-liquid separator 24 (in other words, whether the gas-liquid separator 24 is filled with the liquid to the second height position H2).

Each of the liquid level detection sensors 71, 72 used in the present embodiment is an ultrasonic sensor having a transmitter 71a, 72a and a receiver 71b, 72b that are provided so as to sandwich the gas-liquid separator 24. With the ultrasonic sensor, an ultrasonic wave detected by the receiver 71b, 72b is high when a portion between the transmitter 71a, 72a and the receiver 71b, 72b is filled with the liquid, and an ultrasonic wave detected by the receiver 71b, 72b is low when a gas is present between the transmitter 71a, 72a and the receiver 71b, 72b. Thus, based on the intensity of ultrasonic wave detected by the receiver 71b, 72b, it is possible to detect whether the liquid level has reached the predetermined height position H1, H2 inside the gas-liquid separator 24.

When the ultrasonic sensors are used as both the liquid level detection sensors 71, 72, the transmitters 71a, 72a and the receivers 71b, 72b need to be held while being pressed against the gas-liquid separator 24 so that a gap is not formed between the transmitters 71a, 72a, the receivers 71b, 72b and the gas-liquid separator 24. Thus, in the present embodiment, the blood purification device 1 includes a sensor holder 73 which holds the liquid level detection sensors 71, 72 and to which the gas-liquid separator 24 is attached.

Figure 2A:
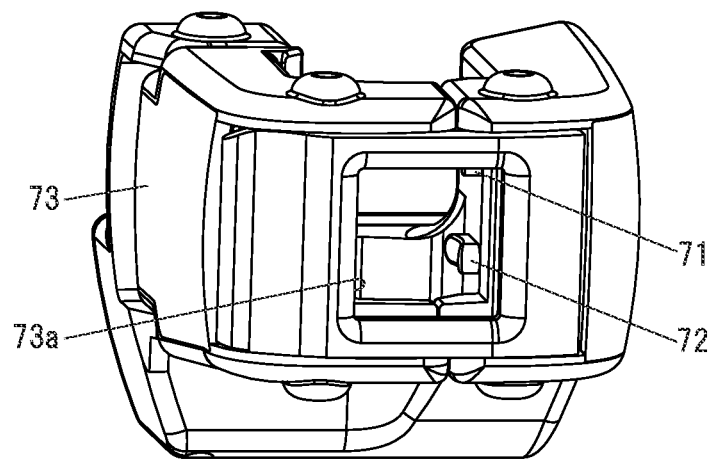
FIG. 2A is a perspective view showing a sensor holder.
Figure 2B:
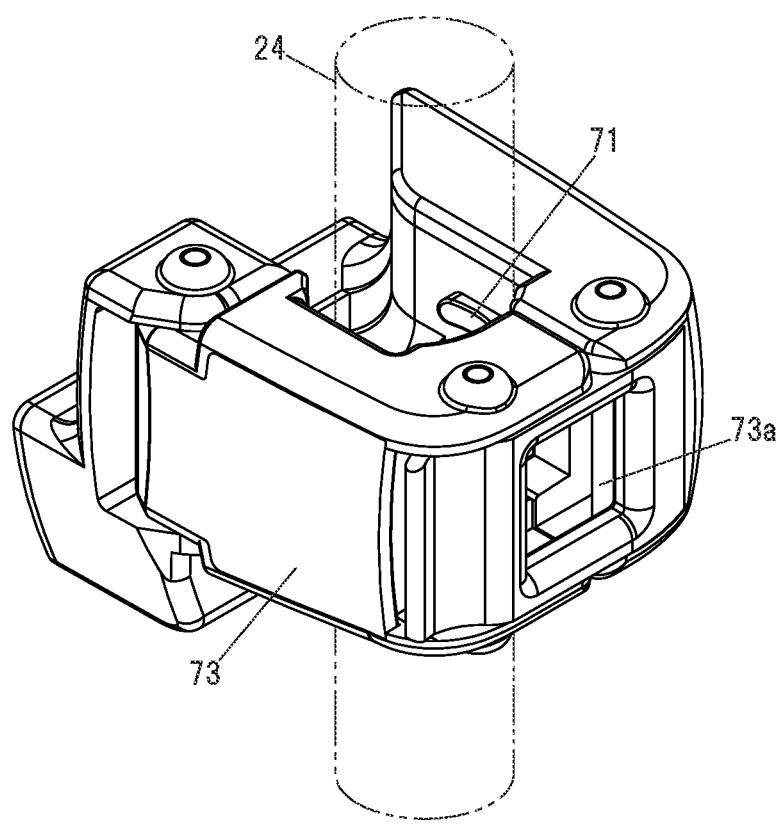
FIG. 2B is a perspective view showing the sensor holder.

As shown in FIGS. 1, 2A and 2B, the sensor holder 73 is attached to cover the circumference of the gas-liquid separator 24. Therefore, in the present embodiment, a window part (an opening) 73a is provided on the front face of the sensor holder 73 so that the liquid level in the gas-liquid separator 24 can be visually checked. In this regard, the sensor holder 73 is attached to the blood purification device 1 so that the front face of the sensor holder 73 is located on the front side of the blood purification device 1 (a surface with which an operator faces the blood purification device 1). The window part 73a should be formed in a position at which it is easy to visually check in a state that the sensor holder 73 is attached to the gas-liquid separator 24, and the size, etc., thereof can be appropriately adjusted. It may be configured to allow the liquid level in the gas-liquid separator 24 to be visually checked by making the sensor holder 73 using a highly transparent member without forming the window part 73a. The transmitters 71a, 72a and the receivers 71b, 72b of the ultrasonic sensors are arranged respectively on one and another of side surfaces of the sensor holder 73. The transmitters 71a, 72a and the receivers 71b, 72b are provided on inner side surfaces of the sensor holder 73 so as to face each other with the gas-liquid separator 24 in-between.

Although the ultrasonic sensors are used as both the liquid level detection sensors 71, 72 in the present embodiment, it is not limited thereto. Optical sensors or capacitive sensors, etc., may be used as both the liquid level detection sensors 71, 72.

The liquid level adjustment mechanism 8 has an air line 81 connected to an upper part of the gas-liquid separator 24, an air filter 82 provided on the air line 81, an air pump 83, and a pressure sensor 84.

The air line 81 is composed of, e.g., a flexible tube, etc. The air pump 83 is composed of a peristaltic pump that squeezes the tube to cause the air to flow. The air pump 83 is connected to the gas-liquid separator 24 via the air filter 82. The air filter 82 is a so-called hydrophobic filter, and is configured to allow gases to pass therethrough but to not allow liquids to pass therethrough (very high resistance to the passage of liquids). The pressure sensor 84 is configured to detect pressure on the air filter 82-side of the air pump 83.

A liquid level control unit 91 for controlling the liquid level height in the gas-liquid separator 24, a sensor abnormality determination unit 92 and a suction abnormality determination unit 93 are mounted on the control device 9. The liquid level control unit 91, the sensor abnormality determination unit 92 and the suction abnormality determination unit 93 are realized by appropriately combining an arithmetic element such as CPU, a memory, a storage device, a software, and an interface, etc.

The liquid level control unit 91 of the blood purification device 1 in the present embodiment performs control so that the liquid level height during priming for passing a physiological saline solution through each circuit is higher than the liquid level height during treatment. In more particular, the liquid level control unit 91 controls the air pump 83 of the liquid level adjustment mechanism 8 while monitoring an output of the first liquid level detection sensor 71 so that, during the treatment, the gas is detected at the first height position H1 and the liquid level height is lower than the first height position H1, and so that, during priming, the gas is not detected at the first height position H1 and the liquid level height is not lower than the first height position H1. As a result, it is possible to sufficiently clean the gas-liquid separator 24 without work of, e.g., turning the gas-liquid separator 24 upside down at the time of priming. It is also possible to reduce the amount of extracorporeally circulated blood by lowering to a liquid level height appropriate for during treatment.

In the present embodiment, the liquid level control unit 91 also controls the air pump 83 of the liquid level adjustment mechanism 8 while monitoring an output of the second liquid level detection sensor 72 so that, during the treatment, the gas is not detected at the second height position H2 and the liquid level height is not lower than the second height position H2, and so that, during blood return for retuning blood to a patient, the gas is detected at the second height position H2 and the liquid level height is lower than the second height position H2. If the liquid level height during blood return is high, the blood and the physiological saline solution may be mixed to each other in the gas-liquid separator 24 when the physiological saline solution for blood return is introduced, and a large amount of physiological saline solution may be required for blood return. By lowering the liquid level height during blood return, it is possible to suppress such a problem, to reduce the amount of physiological saline solution to be used, and to perform the blood return process in a short time.

In this regard, to reduce the amount of extracorporeally circulated blood, the liquid level height during treatment could be reduced to as low as, e.g., the liquid level height during blood return. However, this increases a risk that air bubbles in the blood are not sufficiently separated and removed, resulting in detection of air bubbles by the air bubble detector 25 and interruption of treatment. To suppress the interruption of treatment due to air bubble detection by the bubble detection device 25, the liquid level height during treatment needs to be set to a liquid level height at which air bubbles can be sufficiently separated and removed, while taking into consideration the flow rate of the blood and buoyancy of air bubbles, etc. The liquid level height during priming should be set to higher than "the liquid level height at which air bubbles can be sufficiently separated and removed" described above, and the liquid level height during blood return should be set to lower than "the liquid level height at which air bubbles can be sufficiently separated and removed" described above.

As described above, in the present embodiment, the liquid level height is controlled to be not lower than the first height position H1 during priming, lower than the first height position H1 and not lower than the second height position H2 during treatment, and lower than the second height position H2 during blood return. Hereinafter, the state of the liquid level detection sensors 71, 72 when not detecting the gas (when detecting that it is filled with the liquid) is referred to as ON, and the state when detecting the gas is referred to as OFF. The liquid level control unit 91 adjusts the liquid level height by adjusting the air volume in the gas-liquid separator 24 using the air pump 83 so that both the liquid level detection sensors 71, 72 are ON during priming, the first liquid level detection sensor 71 is OFF and the second liquid level detection sensor 72 is ON during treatment, and both the liquid level detection sensors 71, 72 are OFF during blood return.

Meanwhile, if the liquid level detection sensors 71, 72 fail, the liquid level height adjustment may not be performed in a normal manner, resulting in an unintended problem. Therefore, in the present embodiment, the sensor abnormality determination unit 92 diagnoses whether or not an abnormality is occurring in the liquid level detection sensors 71, 72. The sensor abnormality determination unit 92 calculates (adds up) a liquid level height adjustment amount per unit time (within a preset period of time) based on a history of a liquid level height adjustment operation by the liquid level adjustment mechanism 8, and when a result of the calculation exceeds a predetermined threshold, stops the liquid level height adjustment by the liquid level adjustment mechanism 8 upon determination that there is an abnormality in the liquid level detection sensors 71, 72.

When, e.g., the first liquid level detection sensor 71 fails and is ON all the time, the air is continuously delivered into the gas-liquid separator 24 by the air pump 83 during treatment or blood return, and the liquid level height adjustment amount per unit time is increased. The sensor abnormality determination unit 92 monitors the liquid level height adjustment amount per unit time, and stops the liquid level height adjustment when exceeding a preset threshold.

Meanwhile, if the air filter 82 gets wet for some reason, it is difficult for the air to pass through the air filter 82 and the liquid level height control by the air pump 83 may not be performed in a normal manner. Based on this, in the present embodiment, the suction abnormality determination unit 93 monitors whether or not the air filter 82 is wet. The suction abnormality determination unit 93 stops driving the air pump 83 when a detection value of the pressure sensor 84 becomes lower than a preset abnormality determination pressure (i.e., when pressure is excessively negative) during when the air pump 83 is operated to discharge the air from the gas-liquid separator 24.

The blood purification device 1 also includes an alarm unit 10 that issues an alarm when an abnormality is detected by the sensor abnormality determination unit 92 or the suction abnormality determination unit 93.

The alarm unit 10 has an alarm device 101 that produces light, sound or vibration or displays a warning message on a display such as monitor, and an alarm control unit 102 for controlling the alarm device 101. The alarm device 101 is composed of, e.g., a buzzer emitting a warning tone by sound and a display for displaying a warning message. The alarm control unit 102 causes, e.g., the buzzer to produce sound and the display to show a warning message. The alarm control unit 102 is mounted on the control device 9 and is realized by appropriately combining an arithmetic element such as CPU, a memory, a storage device, a software, and an interface, etc.

(Liquid Level Height Control During Priming)

Figure 3:
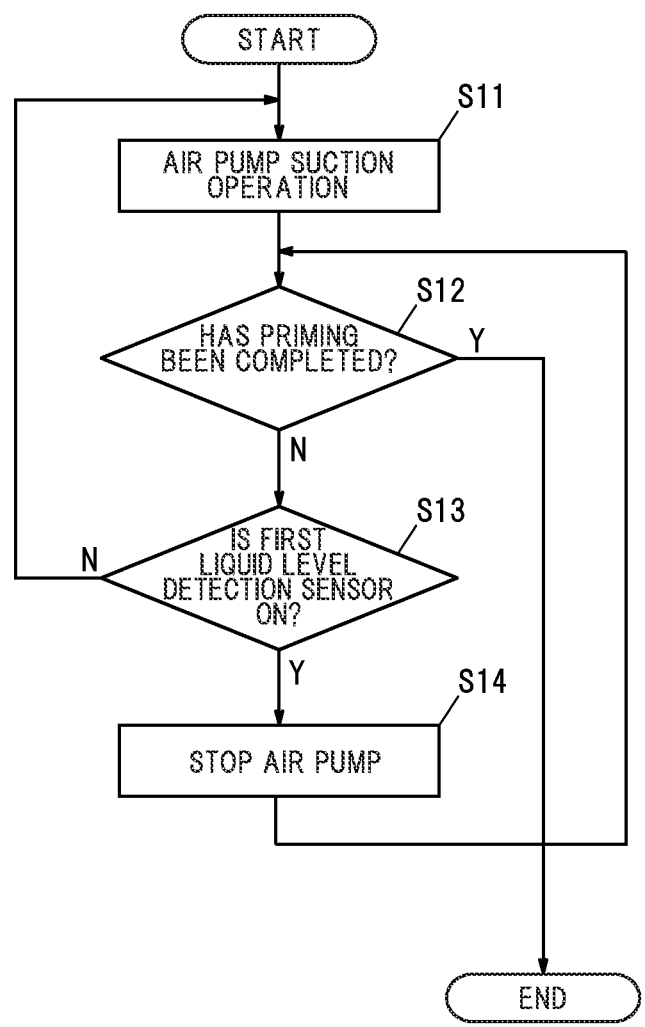
FIG. 3 is a flowchart showing a liquid level height control flow during priming.

FIG. 3 is a flowchart showing a liquid level height control flow during priming. During priming, a bag holding a physiological saline solution is connected to an end of the blood circuit 2 on the vein-side puncture needle 22-side, a waste liquid reservoir is arranged at an end of the blood circuit 2 on the artery-side puncture needle 21-side, and the physiological saline solution in the bag is then introduced into the blood circuit 2. If air enters the blood purifier 3 during priming, it is difficult to remove the air. Therefore, when starting priming, the physiological saline solution is firstly introduced into the gas-liquid separator 24 by driving air pump 83 (sucking operation), and the physiological saline solution is then introduced into the blood circuit 2 on the artery-side puncture needle 21-side relative to the gas-liquid separator 24 by driving the blood pump 23 in a direction opposite to the normal direction during treatment. Hereinafter, an operation for driving the air pump 83 so that the air in the gas-liquid separator 24 is discharged is referred to as suction operation, and an operation for driving the air pump 83 so that the air is introduced into the gas-liquid separator 24 is referred to as discharge operation.

At the time of starting priming, the liquid level control unit 91 implements the control flow of FIG. 3 by being triggered by an operator's operation, etc. Firstly, in Step S11, the physiological saline solution is drawn into the gas-liquid separator 24 by a suction operation of the air pump 83. After that, in Step S12, whether or not priming has been completed is determined. When the determination made in Step S12 is Yes, the process ends.

When the determination made in Step S12 is No, whether the first liquid level detection sensor 71 is ON (whether the liquid fills to the first height position H1) is determined in Step S13. When the determination made in Step S13 is No, the process returns to Step S11 and the air pump 83 continues the suction operation. When the determination made in Step S13 is Yes, the air pump 83 is stopped in Step S14 and the process returns to Step S12.

Although it is not shown in FIG. 3, a process of lowering the liquid level height to the liquid level height for during the treatment (to the liquid level height lower than the first height position H1 and not lower than the second height position H2) may be performed at the time of completion of priming since treatment is performed after completion of priming.

(Liquid Level Height Control During Treatment)

Figure 4:
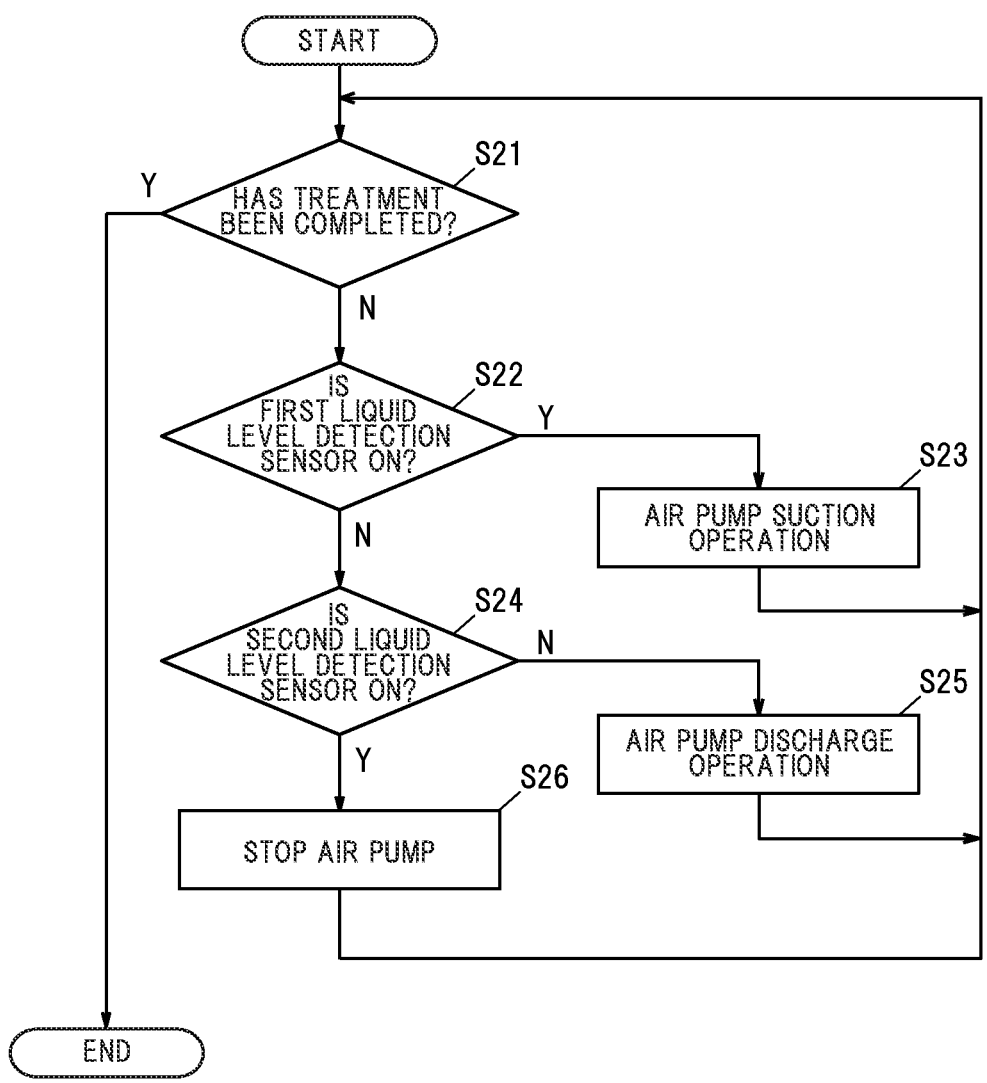
FIG. 4 is a flowchart showing the liquid level height control flow during treatment.

FIG. 4 is a flowchart showing the liquid level height control flow during treatment. At the time of starting treatment, the liquid level control unit 91 implements the control flow of FIG. 4 by being triggered by an operator's operation, etc. Firstly, in Step S21, whether the treatment has been completed is determined. When the determination made in Step S21 is Yes, the process ends. When the determination made in Step S21 is No, whether the first liquid level detection sensor 71 is ON (whether the liquid fills to the first height position H1) is determined in Step S22. When the determination made in Step S22 is Yes, the discharge operation by the air pump 83 is performed in Step 23 and the process returns to Step S21.

When the determination made in Step S22 is No, whether the second liquid level detection sensor 72 is ON (whether the liquid fills to the second height position H2) is determined in Step S24. When the determination made in Step S24 is No, the suction operation by the air pump 83 is performed in Step S25 and the process returns to Step S21. When the determination made in Step S24 is Yes, the air pump 83 is stopped in Step S26 and the process returns to Step S21.

(Liquid Level Height Control During Blood Return)

FIG. 5 is a flowchart showing the liquid level height control flow during blood return. At the time of starting blood return, the liquid level control unit 91 implements the control flow of FIG. 5 by being triggered by an operator's operation, etc. When the blood return is automatically performed after completion of the treatment, the liquid level control unit 91 implements the flow of FIG. 5 at the start of control of such blood return. Firstly, the discharge operation by the air pump 83 is performed in Step S31 to lower the liquid level in the gas-liquid separator 24. After that, in Step S32, whether or not blood return has been completed is determined. When the determination made in Step S32 is Yes, the process ends.

When the determination made in Step S32 is No, whether the second liquid level detection sensor 72 is ON (whether the liquid fills to the second height position H2) is determined in Step S33. When the determination made in Step S33 is Yes, the process returns to Step S31 and the discharge operation by the air pump 83 is continued. When the determination made in Step S33 is No, the air pump 83 is stopped in Step S34 and the process returns to Step S32.

Functions and Effects of the Embodiment

As described above, the blood purification device 1 in the present embodiment includes the liquid level adjustment unit 6 capable of adjusting the liquid level height in the gas-liquid separator 24, and the liquid level adjustment unit 6 performs control so that the liquid level height during priming is higher than the liquid level height during treatment.

Thus, it is possible to sufficiently clean the gas-liquid separator 24 without work of, e.g., turning the gas-liquid separator 24 upside down at the time of priming. As a result, it is easy to perform the priming work and it is possible to easily realize automation of priming. It is also possible to reduce the amount of extracorporeally circulated blood by lowering the liquid level height during treatment. In other words, according to the present embodiment, it is possible to realize the blood purification device 1 capable of suppressing an increase in an amount of blood extracorporeally circulated during treatment while facilitating priming work.

SUMMARY OF THE EMBODIMENT

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A blood purification device (1), comprising: a blood circuit (2) for extracorporeally circulating blood of a patient: a blood purifier (3) provided on the blood circuit (2): a gas-liquid separator (24) being provided on the blood circuit (2) on the downstream side of the blood purifier (3) on a blood flow and separating air bubbles contained in inflowing blood; and a liquid level adjustment unit (6) capable of adjusting a liquid level height in the gas-liquid separator (4), wherein the liquid level adjustment unit (6) performs control so that the liquid level height during priming is higher than the liquid level height during treatment.

[2] The blood purification device (1) described in [1], wherein the liquid level adjustment unit (6) comprises a first liquid level detection sensor (71) being provided at a first height position (H1) of the gas-liquid separator (24) and being capable of detecting whether a gas is present at the first height position (H1) inside the gas-liquid separator (24), a liquid level adjustment mechanism (8) that can adjust the liquid level height by introducing air into the gas-liquid separator (24) or discharging air from the gas-liquid separator (24), and a liquid level control unit (91) controlling the liquid level adjustment mechanism (8) so that, during treatment, the gas is detected at the first height position (H1) and the liquid level height is lower than the first height position (H1), and so that, during priming, the gas is not detected at the first height position (H1) and the liquid level height is not lower than the first height position (H1).

[3] The blood purification device (1) described in [1] or [2], wherein the liquid level adjustment unit (6) further comprises a second liquid level detection sensor (72) being provided at a second height position (H2) lower than the first height position (H1) and being capable of detecting whether a gas is present at the second height position (H2) inside the gas-liquid separator (24), and the liquid level control unit (91) controls the liquid level adjustment mechanism (8) so that, during treatment, the gas is not detected at the second height position (H2) and the liquid level height is lower than the first height position (H1) and not lower than the second height position (H2), and so that, during blood return for retuning blood to a patient, the gas is detected at the second height position (H2) and the liquid level height is lower than the second height position (H2).

[4] The blood purification device (1) described in [2] or [3], wherein the liquid level adjustment unit (6) further comprises a sensor abnormality determination unit (92) that calculates a liquid level height adjustment amount per unit time based on a history of a liquid level height adjustment operation by the liquid level adjustment mechanism (8), and when a result of the calculation exceeds a predetermined threshold, stops liquid level height adjustment by the liquid level adjustment mechanism (8) upon determination that there is an abnormality in the liquid level detection sensor (71, 72).

[5] The blood purification device (1) described in any one of [2] to [4], wherein the liquid level detection sensor (71, 72) comprises an ultrasonic sensor comprising a transmitter (71a, 72a) and a receiver (71b, 72b) that are provided so as to sandwich the gas-liquid separator (24), a sensor holder (73) for holding the liquid level detection sensor (71, 72) is provided and attached to the gas-liquid separator (24), and the sensor holder (73) is configured so that the liquid level in the gas-liquid separator (24) can be visually checked.

[6] The blood purification device (1) described in [5], wherein the sensor holder (73) comprises a window part (73a) on the front face thereof to allow the liquid level in the gas-liquid separator (24) to be visually checked, and the transmitter (71a, 72a) and the receiver (71b, 72b) of the ultrasonic sensor are respectively arranged on one and another of side surfaces of the sensor holder (73).

[7] The blood purification device (1) described in any one of [1] to [6], wherein the liquid level adjustment mechanism (8) comprises an air pump (83) connected to the gas-liquid separator (24) via an air filter (82), and a pressure sensor (84) for detecting pressure on the air filter (82) side of the air pump (83), and the liquid level adjustment unit (6) further comprises a suction abnormality determination unit (93) that stops driving the air pump (83) when a detection value of the pressure sensor (84) becomes lower than a preset abnormality determination pressure during when the air pump (83) is operated to discharge the air from the gas-liquid separator (24).

Although the embodiment of the invention has been described, the invention according to claims is not to be limited the embodiment described above. In addition, all combinations of the features described in the embodiment are not necessary to solve the problem of the invention.

The invention can be appropriately modified and implemented without departing from the gist thereof. For example, although an example in which the peristaltic air pump 83 is used as the liquid level adjustment mechanism 8 has been described in the embodiment, other types of pumps such as, e.g., a cascade type may be used as the air pump 83. It is also possible to omit the air pump 83 by configuring to introduce the gas into the gas-liquid separator 24 from a gas source, or by configuring to introduce the physiological saline solution into the gas-liquid separator 24 at a predetermined inflow pressure by, e.g., providing a bag for holding the physiological saline solution above the gas-liquid separator 24 at the time of priming while allowing the air in the gas-liquid separator 24 to be discharged by an atmospheric relief valve, etc.

REFERENCE SIGNS LIST

1: blood purification device
2: blood circuit
24: gas-liquid separator
3: blood purifier
4: liquid supply circuit
5: waste liquid circuit
6: liquid level adjustment unit
71: first liquid level detection sensor
72: second liquid level detection sensor
71a, 72a: transmitter
71b, 72b: receiver
73: sensor holder
73a: window part
8: liquid level adjustment mechanism
81: air line
82: air filter
83: air pump
84: pressure sensor
9: control device
91: liquid level control unit
92: sensor abnormality determination unit
93: suction abnormality determination unit
H1: first height position
H2: second height position

The invention claimed is:

1. A blood purification device, comprising:
a blood circuit for extracorporeally circulating blood of a patient;
a blood purifier provided on the blood circuit;
a gas-liquid separator being provided on the blood circuit on a downstream side of the blood purifier in a blood flow and separating air bubbles contained in inflowing blood;
a liquid level adjustment unit capable of adjusting a liquid level height in the gas-liquid separator; and
a liquid level control unit controlling the liquid level adjustment unit so that, during treatment, a gas is detected at a first height position and the liquid level height is lower than the first height position, and so that, during priming, the gas is not detected at the first height position and the liquid level height is not lower than the first height position,
wherein the liquid level adjustment unit performs control so that the liquid level height during priming is higher than the liquid level height during treatment; and
wherein the liquid level adjustment unit comprises a first liquid level detection sensor being provided at a first height position of the gas-liquid separator and being capable of detecting whether the gas is present at the first height position inside the gas-liquid separator, the liquid level adjustment unit is capable of adjusting the liquid level height by introducing air into the gas-liquid separator or discharging air from the gas-liquid separator.

2. The blood purification device according to claim 1, wherein the liquid level adjustment unit further comprises a second liquid level detection sensor being provided at a second height position lower than the first height position and being capable of detecting whether the gas is present at the second height position inside the gas-liquid separator, and the liquid level control unit controls the liquid level adjustment unit so that, during treatment, the gas is not detected at the second height position and the liquid level height is lower than the first height position and not lower than the second height position, and so that, during blood return for returning blood to a patient, the gas is detected at the second height position and the liquid level height is lower than the second height position.

3. The blood purification device according to claim 1, wherein the liquid level adjustment unit further comprises a sensor abnormality determination unit that calculates a liquid level height adjustment amount per unit time based on a history of a liquid level height adjustment operation by the liquid level adjustment unit, and when a result of a calculation exceeds a predetermined threshold, stops liquid level height adjustment by the liquid level adjustment unit upon determination that there is an abnormality in the first liquid level detection sensor.

4. The blood purification device according to claim 1, wherein the first liquid level detection sensor comprises an ultrasonic sensor comprising a transmitter and a receiver that are provided so as to sandwich the gas-liquid separator, a sensor holder for holding the first liquid level detection sensor is provided and attached to the gas-liquid separator, and the sensor holder is configured so that the liquid level in the gas-liquid separator can be visually checked.

5. The blood purification device according to claim 4, wherein the sensor holder comprises a window part on a front face thereof to allow the liquid level in the gas-liquid separator to be visually checked, and the transmitter and the receiver of the ultrasonic sensor are respectively arranged on one and another of side surfaces of the sensor holder.

6. A blood purification device, comprising:
a blood circuit for extracorporeally circulating blood of a patient;
a blood purifier provided on the blood circuit;
a gas-liquid separator being provided on the blood circuit on a downstream side of the blood purifier in a blood flow and separating air bubbles contained in inflowing blood; and
a liquid level adjustment unit capable of adjusting a liquid level height in the gas-liquid separator;

wherein the liquid level adjustment unit performs control so that the liquid level height during priming is higher than the liquid level height during treatment, and wherein the liquid level adjustment unit comprises an air pump connected to the gas-liquid separator via an air filter, and a pressure sensor for detecting pressure on an air filter side of the air pump, and the liquid level adjustment unit further comprises a suction abnormality determination unit that stops driving the air pump when a detection value of the pressure sensor becomes lower than a preset abnormality determination pressure during when the air pump is operated to discharge the air from the gas-liquid separator.

7. The blood purification device according to claim 6, wherein the liquid level adjustment unit comprises a first liquid level detection sensor being provided at a first height position of the gas-liquid separator and being capable of detecting whether a gas is present at the first height position inside the gas-liquid separator, the liquid level adjustment unit is capable of adjusting the liquid level height by introducing air into the gas-liquid separator or discharging air from the gas-liquid separator, and the blood purification device comprises a liquid level control unit controlling the liquid level adjustment unit so that, during treatment, the gas is detected at the first height position and the liquid level height is lower than the first height position, and so that, during priming, the gas is not detected at the first height position and the liquid level height is not lower than the first height position.

8. The blood purification device according to claim 7, wherein the liquid level adjustment unit further comprises a sensor abnormality determination unit that calculates a liquid level height adjustment amount per unit time based on a history of a liquid level height adjustment operation by the liquid level adjustment unit, and when a result of a exceeds a predetermined threshold, stops liquid level height adjustment by the liquid level adjustment unit upon determination that there is an abnormality in the first liquid level detection sensor.

9. The blood purification device according to claim 7, wherein the first liquid level detection sensor comprises an ultrasonic sensor comprising a transmitter and a receiver that are provided so as to sandwich the gas-liquid separator, a sensor holder for holding the first liquid level detection sensor is provided and attached to the gas-liquid separator, and the sensor holder is configured so that the liquid level in the gas-liquid separator can be visually checked.

10. The blood purification device according to claim 9, wherein the sensor holder comprises a window part on a front face thereof to allow the liquid level in the gas-liquid separator to be visually checked, and the transmitter and the receiver of the ultrasonic sensor are respectively arranged on one and another of side surfaces of the sensor holder.

11. The blood purification device according to claim 7, wherein the liquid level adjustment unit further comprises a second liquid level detection sensor being provided at a second height position lower than the first height position and being capable of detecting whether a gas is present at the second height position inside the gas-liquid separator, and the liquid level control unit controls the liquid level adjustment unit so that, during treatment, the gas is not detected at the second height position and the liquid level height is lower than the first height position and not lower than the second height position, and so that, during blood return for returning blood to a patient, the gas is detected at the second height position and the liquid level height is lower than the second height position.

12. The blood purification device according to claim 6, wherein the liquid level adjustment unit further comprises a liquid level detection sensor being provided at a second height position lower than a first height position and being capable of detecting whether a gas is present at the second height position inside the gas-liquid separator, and a liquid level control unit controls the liquid level adjustment unit so that, during treatment, the gas is not detected at the second height position and the liquid level height is lower than the first height position and not lower than the second height position, and so that, during blood return for returning blood to a patient, the gas is detected at the second height position and the liquid level height is lower than the second height position.

* * * * *